(12) United States Patent
Sibbitt et al.

(10) Patent No.: US 6,385,479 B1
(45) Date of Patent: May 7, 2002

(54) METHOD FOR DETERMINING ACTIVITY IN THE CENTRAL NERVOUS SYSTEM

(75) Inventors: Wilmer L. Sibbitt; William M. Brooks; Helen Petropoulos, all of Albuquerque, NM (US)

(73) Assignee: Science & Technology Corporation @ UNM, Albuquerque, NM (US)

( * ) Notice: Subject to any disclaimer, the term of this patent is extended or adjusted under 35 U.S.C. 154(b) by 0 days.

(21) Appl. No.: 09/541,022

(22) Filed: Mar. 31, 2000

Related U.S. Application Data

(60) Provisional application No. 60/127,302, filed on Mar. 31, 1999.

(51) Int. Cl.[7] ............................................... A61B 5/055
(52) U.S. Cl. ......................... 600/410; 324/307; 324/309
(58) Field of Search .......................... 600/410; 324/307, 324/309; 436/173

(56) References Cited

U.S. PATENT DOCUMENTS

| | | | |
|---|---|---|---|
| 4,332,566 A | | 6/1982 | Mazeski et al. |
| 5,111,819 A | | 5/1992 | Hurd |
| 5,200,345 A | | 4/1993 | Young |
| 5,218,529 A | | 6/1993 | Meyer et al. |
| 5,357,959 A | | 10/1994 | Fishman |
| 5,617,861 A | | 4/1997 | Ross et al. |
| 5,644,232 A | * | 7/1997 | Smith |
| 5,647,361 A | * | 7/1997 | Damadian |
| 5,818,231 A | * | 10/1998 | Smith |
| 5,887,588 A | | 3/1999 | Usenius et al. |
| 6,090,408 A | * | 7/2000 | Li et al. |
| 6,249,594 B1 | * | 6/2001 | Hibbard |

\* cited by examiner

*Primary Examiner*—Marvin M. Lateef
*Assistant Examiner*—Runa Shah Qaderi
(74) *Attorney, Agent, or Firm*—Jaqtiani & Guttag

(57) ABSTRACT

The present invention provides a method for determining whether an individual has a central nervous system disease or injury comprising: obtaining a $T_2$ measurement for at least one brain tissue sample from an individual; determining if the $T_2$ measurement indicates the presence of a central nervous system disease or injury in the individual. The present invention also provides a method for determining whether an individual has a central nervous system disease or injury comprising: obtaining a first $T_2$ measurement using an MRI technique for a brain tissue sample from an individual at a first time; obtaining a second $T_2$ measurement using an MRI technique for the brain tissue sample from the individual at a second time; and comparing the second $T_2$ measurement to the first $T_2$ measurement. In addition, the present invention provides a method for determining the effectiveness of a treatment for a central nervous system disease or injury comprising: obtaining a first $T_2$ measurement using an MRI technique for a brain tissue sample from an individual at a first time; administering a first treatment to an individual; obtaining a second $T_2$ measurement using the MRI technique for the brain tissue sample from the individual after administering the first treatment; and comparing the second $T_2$ measurement to the first $T_2$ measurement.

18 Claims, 6 Drawing Sheets

METHOD FOR DETERMINING ACTIVITY IN THE CENTRAL NERVOUS SYSTEM

CROSS-REFERENCE TO RELATED APPLICATIONS

This application makes reference to Provisional Patent Application No. 60/127,302 entitled "Segmentation of Brain Tissues to Calculate T2 (spin-spin) Relaxation to Diagnose Disease of the Brain and Determine Disease Activity" filed Mar. 31, 1999, the entire contents and disclosure of which is hereby incorporated by reference.

GOVERNMENT INTEREST STATEMENT

This invention is made with government support under Grant Number RO1 NS35708 entitled "The Pathophysiology of Neuropsychiatric Systemic Lupus Erythematosus" awarded by the NIH National Institute of Neurologcial Diseases and Stroke. The government may have certain rights in this invention.

BACKGROUND OF THE INVENTION

1. Field of the Invention

The present invention relates to magnetic resonance imaging techniques.

2. Description of the Prior Art

Magnetic resonance imaging (MRI) is a powerful technology that provides clinical images with improved resolution and superior diagnostic value over computed tomography, particularly when applied to brain. Magnetic resonance images are created by processing and displaying digital information in the form of two dimensional or three dimensional displays, which are then subjectively, semi-objectively, or objectively interpreted by observers. The MR technology that produces images also creates quantitative MR data (including proton density, spin-lattice relaxation ($T_1$), spin-spin relaxation ($T_2$), and other factors that influence MR relaxation) that provide important information concerning the physical state of water in normal and pathologic tissues. However, certain diseases and conditions, especially reversible encephalopathies, low grade brain disease, drug effects, or diffuse brain disease may be very difficult or impossible to diagnose or detect using conventional MR techniques. Currently, these brain states can be detected by 1) cerebrospinal fluid analysis, 2) single photo emission tomography (SPECT), positron emission tomography (PET), electroencephalography (EEG), or magnetoencephalography (MEG). Although present in all conventional MRI sequences, quantitative digital data are usually lost or only poorly exploited during the process of image creation and in the subsequent interpretation by the radiologist or other clinical observer.

SUMMARY OF THE INVENTION

It is therefore an object of the present invention to provide MRI techniques that exploit the quantitative nature of magnetic resonance (MR) data, combined with image processing techniques, to determine quantitative digital data in pure brain tissues.

It is another object of the present invention to use quantitative digital data obtained in pure brain tissues to determine the properties of brain tissues, and especially gray matter which is exquisitely sensitive to and more diagnostic of active brain disease relative to white matter or lesional tissues.

It is yet another object of the present invention to provide MR techniques that provide powerful diagnostic information in a wide variety of disease states and provide a MR method for measuring active brain disease previously detectable by CSF analysis, SPECT, PET, EEG or MEG.

It is yet another object of the present invention to provide an MRI technique that broadly expands the power of MRI for the diagnosis and management of disease, yet does not necessarily require high MRI field strengths (greater than 1.5 Tesla) or strong field gradients (as is required in echo planar MR), and thus can be performed on a both simple, inexpensive low field units as well as expensive high-field, high-gradient units. Thus, this technique should make powerful MRI diagnosis more available even to centers with limited resources.

According to a first broad aspect of the present invention, there is provided a method for determining whether an individual has a central nervous system disease or injury comprising: obtaining a $T_2$ measurement for at least one brain tissue sample from an individual; determining if the $T_2$ measurement indicates the presence of a central nervous system disease or injury in the individual.

According to a second broad aspect of the invention, there is provided a method for determining whether an individual has a central nervous system disease or injury comprising: obtaining a first $T_2$ measurement using an MRI technique for a brain tissue sample from an individual at a first time; obtaining a second $T_2$ measurement using an MRI technique for the brain tissue sample from the individual at a second time; and comparing the second $T_2$ measurement to the first $T_2$ measurement.

According to a third broad aspect of the invention, there is provided a method for determining the effectiveness of a treatment for a central nervous system disease or injury comprising: obtaining a first $T_2$ measurement using an MRI technique for a brain tissue sample from an individual at a first time; administering a first treatment to an individual; obtaining a second $T_2$ measurement using the MRI technique for the brain tissue sample from the individual after administering the first treatment; and comparing the second $T_2$ measurement to the first $T_2$ measurement.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Figure 1:
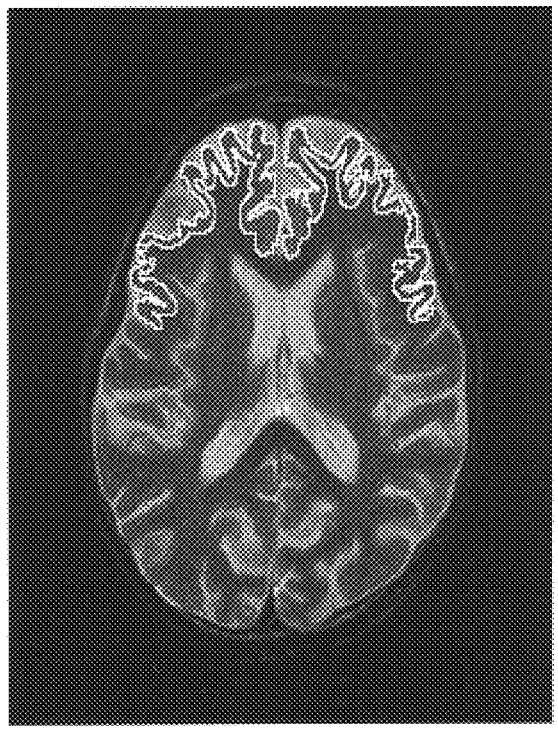
FIG. 1 shows the output of a segmentation routine of the present invention applied to segment frontal gray matter from a patient with active NPSLE.

It is advantageous to define several terms before describing the invention. It should be appreciated that the following definitions are used throughout this application.

Where the definition of terms departs from the commonly used meaning of the term, the definitions provided below should be used in interpreting the present invention, unless specifically indicated otherwise.

For the purposes of the present invention, the term "individual" refers to either an individual person or animal.

For the purposes of the present invention, the term "MRI technique" refers to any technique using MRI to analyze an individual's brain.

For the purposes of the present invention, the term "brain sample" refers to a digital representation of a portion of an individual's brain. A portion of an individual's brain may include an individual's entire brain.

For the purposes of the present invention, the term "segmentation technique" refers to any technique using segmentation to analyze an individual's brain.

For the purposes of the present invention, the term "central nervous system disease" refers to any disease that originates in an individual's central nervous system or a disease where central nervous systemic disease is the major clinical manifestation of the disease. Examples of central nervous system diseases include: Amyotrophic Lateral Sclerosis, Multiple Sclerosis (MS), Alzheimer's Disease, Traumatic Brain Injury, Stroke, Ischemic Brain Disease, Psychiatric Disorders, and reversible or metabolic encephalopathies, including hepatic encephalopathy, hypoxia, drug or toxin-related encephalopathies and others, etc. In contrast, a systemic disease, such as Systemic Lupus Erythematosis (SLE), where the most obvious manifestations are usually not in the central nervous system is not a central nervous system disease, because Lupus predominately targets other areas of the body and only secondarily affects an individual's central nervous system.

For the purposes of the present invention, the term "central nervous system injury" refers to any physical, metabolic, toxic, chemical, or immunologic injury to an individual's central nervous system that affects the functioning of the individual's central nervous system. An example of a central nervous system injury is traumatic brain injury.

For the purposes of the present invention, the term "neurodegenerative disease" refers to any central nervous system disease that primarily affects central nervous system neurons, wherever the neurons are found. One example of such a neurodegenerative disease is Amyotrophic Lateral Sclerosis which is a progressive neurodegenerative disease that primarily affects motor neurons in the cerebral cortex, brain stem, and spinal cord. Other examples of neurodegenerative diseases include Alzheimer's disease, aging, congenital metabolic dystrophies, including mitochondrial dystrophies, etc.

For the purposes of the present invention, the term "brain functioning" refers to any conventional measure of brain functioning including: intelligence, intelligence quotient, electrical brain activity, etc.

For the purposes of the present invention, the term "standard brain functioning" refers to the normal brain functioning of individuals similar to the individual whose brain functioning is being determined. For example, an individual who is 6 years old could have her brain functioning compared against the standard brain functioning of other 6 year olds, i.e. the typical brain functioning of other 6 year olds for the particular brain functioning being determined for an individual. Such comparisons may be necessary where an individual's brain functioning has not been previously measured prior to determining the individual's current brain functioning.

For the purposes of the present invention, the term "administering a treatment" includes any form of treatment administered to an individual in an attempt to reduce or mitigate the effects of a central nervous system disease or injury. Examples of administering a treatment including administering a drug treatment to an individual, performing an intervention, etc.

For the purposes of the present invention, the term "drug" refers to any type of substance that is commonly considered a drug. For the purposes of the present invention, a drug may be a substance that acts on the central nervous system of an individual, e.g. a narcotic, hallucinogen, barbiturate, or a psychotropic drug. For the purposes of the present invention, a drug may also be a substance that kills or inactivates disease-causing infectious organisms. In addition, for the purposes of the present invention, a drug may be a substance that affects the activity of a specific cell, bodily organ or function. A drug may be an organic or inorganic chemical, a biomaterial, etc.

For the purposes of the present invention, a "intervention" may be any procedure, therapy, maneuver, counseling, physical force (pressure, magnetic, electrical, acupuncture), supplement (dietary, diet, herbal,) that directly or indirectly acts on the central nervous system of an individual to cause some change in disease, behavior, mood, or other brain function.

Description

The techniques of the present invention exploit the quantitative nature of MR data, which, when combined with image processing techniques to determine quantitative values in pure tissues, are useful for determining the properties of brain tissues, and especially gray matter which is exquisitely sensitive to and more diagnostic of active brain disease relative white matter or lesional tissues. As shown below, these techniques provide powerful diagnostic information in a wide variety of disease states and provide a MR method for measuring active brain disease previously detectable by CSF analysis, SPECT, PET, EEG, MEG, or MR techniques that require high magnetic field strengths or strong gradients (as in echo planar systems). These techniques broadly expand the power of MRI for the diagnosis and management of disease.

Magnetic resonance imaging (MRI) is a powerful technology that provides clinical images with improved resolution and superior diagnostic value over computed tomography, particularly when applied to brain. Magnetic resonance images are created by processing and displaying digital information in the form of two dimensional or three dimensional displays, which are then subjectively, semi-objectively, or objectively interpreted by observers. The MR technology that produces images also creates quantitative MR data (including proton density, spin-lattice relaxation ($T_1$), and spin-spin relaxation ($T_2$) that provide important information concerning the physical state of water in normal and pathologic tissues. Although present in all conventional MRI sequences, the quantitative digital data are usually lost or only poorly exploited during the process of image creation and in the subsequent interpretation by the radiologist observer. The combination of image processing (gray and white matter segmentation) to calculate precise $T_2$ values has powerful, new clinical applications which markedly increase the sensitivity and specificity of conventional MRI for detecting disease and quantifying disease activity. This invention describes new quantitative technologies which can be used to produce diagnostic products with immediate applications to clinical medicine and biomedical research as will become apparent to those skilled in the art.

The present invention provides quantitative measures of $T_2$ in discrete brain tissues defined by image processing techniques (tissue segmentation) and uses these quantitative values to diagnose brain disease and determine disease activity with specific applications to health care, research, and industry.

The diagnostic ability of MRI in brain diseases has been improved by the application of image processing (segmentation of gray and white matter) to provide quantitative measures of $T_2$ which have special value in the diagnosis of disease. The present invention includes the following novel features: 1) segmentation of gray matter and tissues using a number of different techniques, 2) exclusion of partial volume artifacts, 3) calculation of $T_2$ on a pixel by pixel basis using conventional mathematical formulae, 4) use of the $T_2$ values—primarily of gray matter—to diagnose specific diseases, and 5) pixel histogram analysis to determine the pattern of involvement. Powerful data is provided below that confirms both the uniqueness and the particular value of these specific measures to diagnose brain disease and brain disease activity. This invention has wide applicability to the diagnosis of disease, particularly inflammatory, metabolic, and post-traumatic brain disease.

Magnetic resonance imaging is one of the most advanced and reliable methods to image water or fat-containing tissues in the human body. The primary strength of MRI is the ability to detect visible structural changes, rather than the potential for making precise and accurate quantitative measurements of the chemical and physiologic processes of the living body. The quantitative power of MRI is further limited by the primary demand for clinical images, which reduce digital data to visual, essentially analog representations, to be interpreted by the radiologist. Accurate, reproducible interpretation relies on observer experience, bias, and subjectivity. Further, the human observer is unable to recognize subtle changes in image intensity, particularly when discrete borders between normal and abnormal tissues are lacking. Accurate, reproducible interpretation of such analog imaging data is completely dependent on the clinical judgement and experience of the radiologist. Despite the power and utility of MRI, the quantitative capabilities of this technology are underutilized and generally unappreciated.

Currently, efforts are underway to automate the radiological interpretation of MR and similar imaging forms. This automation should help standardize MR interpretation, but does not address the problem of the profound loss of biophysical information that occurs during the conversion of digital data into images and the subsequent clinical interpretation. Information that is inherent in conventional images or which can be extracted from a series of conventional images includes proton density, spin-lattice relaxation ($T_1$), and spin-spin relaxation ($T_2$) rates among other measures. Currently, this information—although available with straightforward mathematical processing—is not routinely utilized because: 1) many radiologists and referring clinicians are yet to be convinced that this information is important; 2) few pathologic conditions have been reported where this information is convincingly useful for diagnosis see Whittall, et al. "In Vivo Measurement of T2 Distributions and Water Contents in Normal Human Brain" in MRM, (1997), 37:34–43; and 3) technical difficulties prevent this information from being obtained in a reproducible fashion from specific structures. Important technical difficulties that prevent ready access to quantitative measures include 1) inadequate image processing methodology to define structures of interest from complex images, 2) optimization of image acquisition to provide data that allow superior quantitative measurement and definition of structure, 3) methods to examine patterns and microstructure of diseased tissues, and 4) knowledge of those structures most likely to reflect disease processes not obvious by conventional MR imaging.

There is currently no well accepted, reliable diagnostic tool for measuring disease activity in most brain diseases. Although in diseases such as systemic lupus erythematosus (SLE) there is a scoring system for overall systemic disease activity (SLEDAI—SLE Disease Activity Index), there is no accepted instrument for quantifying the cerebral component of disease. Moreover, the measures that do exist are extremely subjective, relying on physician judgement and experience. The presence of a robust tool for determining subclinical disease and quantifying brain disease activity would provide new objectivity and reliability for new interventional trials and patient management. Precise measurement of $T_2$ in gray matter (GM) and focal lesions reflects disease activity in neuropsychiatric systemic lupus erythematosus (NPSLE), see Sibbitt, et al., "Spin-spin relaxation of brain tissues in systemic lupus erythematosus" in *Arth & Rheum*, (1995), 38:810–818. Preliminary studies, which describe innovative image segmentation methods to precisely define tissues from which the relaxation properties of water can be measured, reveal unsuspected disease activity in a number of disorders that primarily affect the brain.

There is considerable demand, particularly in medical research fields but also in the patient care environment, for methods to transform conventional MR imaging, which relies primarily on subjective interpretation, into an exact science which will provide precise and accurate quantitative measures of clinical importance. The present invention addresses one aspect pertinent to diagnostic power of MRI. Digital information contained in conventional MR images is sensitive to pathologic processes of profound clinical importance, yet these data are not available to and cannot be detected by the radiologist with conventional image interpretation.

MRI can detect typical pathology including focal and diffuse hyperintense lesions, infarcts, hemorrhage, and atrophy with greater sensitivity than computed tomography (see Sibbitt, et al., "Magnetic resonance and CT imaging in the evaluation of acute neuropsychiatric disease in systemic lupus erythematosus" in *Ann Rheumat Dis*, (1989), 48:1014–1022., and Sewell, et al., "Magnetic resonance imaging vs. computed tomographic scanning in neuropsychiatric systemic lupus erythematosus" in *Am J Med*, (1989), 86:625–626. Although MRI provides excellent anatomic detail, interpretation is limited by the experience and objectivity of the observer, the discrimination of the human eye, and the inherent image contrast. MRI can provide quantitative data regarding the relaxation properties of water in different chemical environments induced by inflammatory diseases of the brain, see, Karlik, et al., "NMR studies in experimental allergic encephalomyelitis: Factors which contribute to $T_1$ and $T_2$ values." in *Magn Reson Med*, (1990), 14:1–11. The spin-lattice ($T_1$) and spin-spin relaxation times ($T_2$) provide information regarding the total water in brain, the compartmentalization of brain water, and the degree of association between this water and macromolecules such as myelin and protein see Koenig, et al., "Relaxometry of brain: Why white matter appears bright in MRI" in *Magn Reson Med*, (1990), 14:482–495, and MacKay, et al., "In Vivo Visualization of Myelin Water in Brain by Magnetic Resonance" MRM, (1994), 31:673–677. The total quantity of water (proton density), $T_1$, and $T_2$ are responsible for the image intensity in both normal and abnormal tissues. Pathological processes which are often seen in active NPSLE and other brain diseases—including inflammation, infarction, and edema—usually increase $T_2$. Using quantitative methods, it may be shown that $T_2$ is elevated in normal-appearing gray and white matter of SLE patients and other patients with inflammatory brain disease see, Sibbitt, et al., "Spin-spin relaxation of brain tissues in systemic lupus erythematosus" in *Arth & Rheum*, (1995), 38:810–818. Precise measurement of the $T_2$ of cerebral lesions and normal-appearing brain in SLE demonstrated that quantitative $T_2$ determination extends the utility and sensitivity of conventional MRI in the detection of different forms of NPSLE. A major impediment of this technique is the extremely laborious manual measurements for selecting normal-appearing gray matter, white matter, and lesions which are clearly unrealistic for most research and all clinical diagnostic studies. The present invention concerns the use of automatic and semi-automatic (operator supervised) image processing techniques to segment gray matter, white matter, and lesional tissue to provide precise measures of $T_2$ which are then uniquely and specifically used to diagnose disease and disease activity.

It has now been discovered that $T_2$ measurements may be used to determine whether an individual has Amyotrophic Lateral Sclerosis, a central nervous system disease, and, specifically, a neurodegenerative type of disease. The present invention encompasses using elevated $T_2$ measurements to determine whether an individual has a central nervous system disease.

Amyotrophic Lateral Sclerosis which is a progressive neurodegenerative disease that primarily affects motor neurons in the cerebral cortex, brain stem, and spinal cord. Quantitative $T_2$ determination from clinical $T_2$-weighted imaging series may yield valuable data about disease state and may be a measure of both acute and chronic injury.

$T_2$ may be used to evaluate hippocampal sclerosis, concomitant with gliosis and neuronal cell loss, in patients with temporal lobe epilepsy.

The method of the present invention allows for the use of automated segmentation of brain tissues to be combined with calculation of $T_2$ to diagnose disease and disease activity based on the changes of $T_2$ in brain tissues such as gray matter and lesions. Methods of image segmentation include, but are not restricted to supervised and unsupervised classification techniques, edge detection, neural networks, and fuzzy logic. The method of the present invention may be used to determine the $T_2$ of gray matter, white matter, and lesions in SLE, multiple sclerosis, hepatic encephalopathy, head trauma, and other diseases or physi-ologic states of the brain. Pixel histogram analysis may be used to determine the pattern of gray matter, white matter, and lesional $T_2$ change. The method of the present invention may be used diagnostic, research, therapeutic, formal, and informal venues.

According to the method of the present invention, a $T_2$ measurement for a brain tissue sample, preferably a motor cortex sample, of at least 88 ms, preferably 90 ms, is indicative that an individual is suffering from a central nervous system disease or injury. Based on the data described below, it appears that an individual who is not suffering from central nervous system disease or injury will normally have a $T_2$ brain tissue measurement in gray matter less than 88 ms. The present invention has particular utility in being able to determine if an individual is suffering from early stage ALS. It should be realized that the T2 limits claimed above are derived from a specific example method which results in a T2 estimate, and that minor variations such as multipoint acquisitions rather than two or one point acquisitions, variation in echo time and repetition time, slice thickness variations, use of multiexponential models rather than monexponential models, the choice of segmentation method, partial volume exclusion, editing, and the averaging method (mean, median, mode, trimming algorithm) may result in minor variations in the above T2 value or in the reproducibility of this value, but when the method is standardized in these parameters across a study group will result in reproducible values with just such a normal-abnormal limit with only minor variation from the value claimed above.

Also, the present invention may be used to observe the progress of a central nervous system disease or injury, In general, if several brain tissue $T_2$ measurements, taken over a period of time, are compared for an individual, a increase in an individual's brain tissue $T_2$ measurement is indicative of an increase in the effects of a disease or injury. Conversely, a reduction in an individual's brain tissue $T_2$ measurement is indicative that an individual is recovering from a central nervous system disease or injury.

In addition, the present invention may be used to test the effectiveness of a drug treatment or other clinical intervention, for a central nervous system disease or injury. A brain tissue $T_2$ measurement, preferably a motor cortex $T_2$ measurement, may be taken of an individual prior to a particular drug or treatment being given to an individual. After the individual has been medicated or treated, one or more subsequent brain tissue $T_2$ measurements, preferable motor cortex $T_2$ measurements, may taken to determine if intervention has been effective in treating the central nervous system disease or injury. A reduction in one or more brain tissue $T_2$ measurements after treatment as compared to the brain tissue $T_2$ measurement before treatment is indicative of a particular drug or intervention being effective. When a particular drug or set of drugs or other intervention is given to an individual several times, one or more brain tissue $T_2$ measurements may be taken of the individual to determine the effects of each subsequent treatment.

The following examples illustrate the various steps required to determine a clinically useful measure of $T_2$. They also show that $T_2$ is useful in several example diseases including but not limited to systemic lupus erythematosus, hepatic encephalopathy, multiple sclerosis, and head trauma (traumatic brain injury). They also show that the clinically useful T2 measurement is not a result of sampling artifact resulting from such processes as brain atrophy associated with progressive disease injury.

Although an MRI field strength of 1.5 Tesla is used in the following examples, the present invention encompasses using various MRI field strengths to obtain $T_2$ measurements. The particular $T_2$ measurements indicating whether an individual has a central nervous system disease or injury will depend on the MRI field strength used. However, the relationships between $T_2$ measurements obtained using different field strengths is well known among MRI researchers. Therefore, the particular $T_2$ measurements indicating a central nervous system disease or injury for MRI field strengths other than 1.5 Tesla may be easily extrapolated from the results described in the below examples.

EXAMPLE 1

Image Processing to Segment Gray Matter, White Matter, and Lesions—Method 1: Subtraction/Addition of Image Pairs with k-means Clustering Results demonstrating the unsuspected abnormalities in $T_2$ in SLE were obtained using a laborious manual method (employing 80 measurements per patient) for selecting normal-appearing gray matter, a process which typically took well over two hours to develop a $T_2$ number for an individual patient see Sibbitt, et al., "Spin-spin relaxation of brain tissues in systemic lupus erythematosus" in Arth & Rheum, (1995), 38:810–818, the entire contents and disclosure of which is hereby incorporated by reference. To reduce processing time, automate the procedure, and remove observer bias a robust procedure has been developed for segmenting gray matter (GM), white matter (WM), and cerebrospinal fluid (CSF) and for separating pixels which arise from the interface between tissue types i.e., from volume averaging between e.g. CSF and GM or between GM and WM. The method provides data that correlate closely with the tedious manual method which had been used previously, see Sibbitt, et al., "Spin-spin relaxation of brain tissues in systemic lupus erythematosus" in Arth & Rheum, (1995), 38:810–818, but is vastly superior both in terms of time requirements and that it allows sophisticated pixel histogram analysis. This method is based on linear combinations of the perfectly registered proton density (PD)/$T_2$-weighted image pairs, see Petropoulos, et al., "Elevated $T_2$ of gray matter in systemic lupus erythematosus determined by automated segmentation and histogram analysis" in Proc Int Soc Magn Reson Med 4th Scientific Meeting, New York, (1996). Using this approach lesions may also be identified. Subtraction of these image pairs results in an image with the CSF appearing strongly hypointense while lesions in white matter are isointense with the neighboring brain tissue. The image resulting from the addition of the pair shows the lesions hyperintense. Thus in this approach, two images are generated by: 1) digital subtraction ($D_{sub}$) of the $T_2$-weighted image from the PD image to produce an image which accentuates pixels with partial volume CSF, and 2) digital addition ($D_{add}$) of the $T_2$-weighted image to the PD image to produce an image with partial volume gray/white matter accentuated. A k-means clustering algorithm was used to classify each of the hybrid images producing the segmented anatomy, with each of the output clusters corresponding to a different tissue type. The k-means algorithm is an unsupervised method of classifying images providing an automated method for segmenting images into anatomic subtypes with the operator selecting the number of clusters. FIG. 1 shows the output of this segmentation routine applied to segment frontal GM from a patient with active NPSLE. The regions of obvious CSF/GM partial volume are clearly excluded. Segmenting $D_{sub}$ using 5 clusters defines CSF and partial volume CSF, while 12 clusters for $D_{add}$ is optimal for defining various levels of gray matter and white matter. Labeled clusters corresponding to anatomic structures are identified interactively by selecting a tissue type from the labeled k-means image. From $D_{sub}$, a binary is formed consisting of total gray and white matter, devoid of CSF and partial volume CSF. $D_{add}$ produces a binary consisting of GM, but with partial volume gray/white removed. The two binary images are logically ANDed to produce a binary consisting of pure GM. The region of the frontal lobe is manually masked off from this image and used for the $T_2$ calculations.

Figure 2:
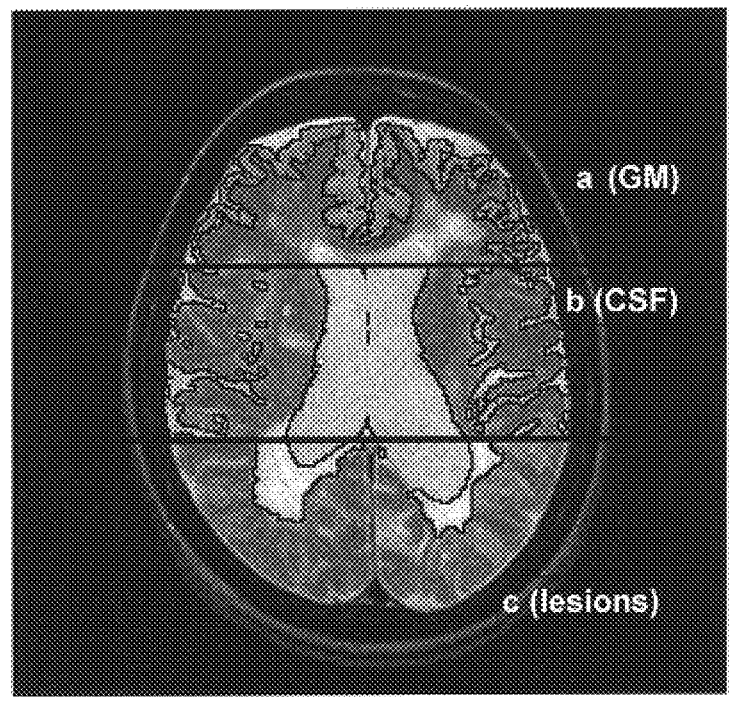
FIG. 2 illustrates the segmentations of the present invention available from a $T_2$-weighted image slice.

FIG. 2 summarizes the segmentations available from a $T_2$-weighted image slice—CSF, lesions, and gray matter. For display purposes, the image is divided into 3 distinct regions by horizontal lines. However, any or all of the 3 analyses can be applied across the whole brain. As discussed above, Section (a) shows the segmentation of pure GM. Section (b) shows specific segmentation of CSF with exclusion of both GM and WM, and Section (c) shows large periventricular lesions clearly segmented from adjacent normal tissues and CSF.

EXAMPLE 2

Image Processing to Segment Gray Matter, White Matter, and Lesions—Method 2: Segmentation of Structures in Noisy MR Images Using Low Pass Filter and Difference Recursive Filter Algorithms The anatomic boundaries of the sural nerve—a small nerve often comprising only 3 or 4 pixels—in the ankles of diabetic patients and controls, see Koechner, et al., "Segmentation of small structures in MR images: Semiautomated tissue hydration measurement" in J Magn Reson Imag (1995) 5:347–352.

The problem was to segment small structures in noisy images. This is a problem because Median and low pass filter techniques which are often used for improving signal-to-noise prior to further analysis were found to blur the anatomy by removing excess edge information. A speckle noise filter was applied based on the Eight Hull Algorithm to remove spurious noise without sacrificing critical nerve boundary information. An automated edge detector was developed based on the difference recursive filter algorithms that produced excellent edge localization, providing a tool to detect narrow lines and edges with weak contrast that is less sensitive to noise than many other edge detectors. This technology is very useful in brains with complex anatomy due to extensive overlapping lesional tissues and is an alternative method to define structures than that detailed above.

EXAMPLE 3

Image Processing to Segment Gray Matter, White Matter, and Lesions—Alternative Methods to Accomplish the Same Purpose Alternative methods can also be used to segment brain tissues and are also claimed as integral to this invention, including but not limited to:
1. Morphologic Segmentation:
    Morphologic segmentation can be performed after features of interest have been binarized and allows ease of transition from 2D to 3D segmentation.
2. Supervised Classification:
    Supervised classification is achieved through the use of multi-spectral information which comes readily from conventional MRI images. Multiple representations (in the form of different MRI acquisitions) of the same slice are plotted in feature space, where like tissues cluster. This type of classification requires the user to "train" the algorithm. This is done by defining regions of interest to which the classifier will assign a voxel. Users may define classes from the plotted clusters or from any of the original images. Following are some examples: Gaussian clustering, Neural Network, Nearest Neighbor, K-Nearest Neighbor, Bayes classifiers, and Parzen Windows.

3. Unsupervised Classification:

Unsupervised classification takes place without the need for a user to predefine classes. The k-means algorithm described in Example 1 is an example of such a classifier. Additional algorithms include the chain method, which places voxels in classes depending on their Euclidean distance from class centroids. The ISODATA (Iterative Self-Organizing Data Analysis) algorithm takes the output of a k-means image and further redefines the segmentation by merging clusters that meet predefined user limits, see Ball, et al, "ISODATA, an iterative methods multivariate data analysis and pattern classifications" in *IEEE International Communications conference*, Philadelphia, June, 1966.

4. Alternative Methods:

The use of fuzzy logic is finding increasing use in the area of MRI segmentation. Algorithms such as fuzzy c-means (the fuzzy version of k-means) place voxels in classes using principles based on fuzzy logic and eliminating the guess factor, see Bezdek, et al, "Review of MR image segmentation techniques using patter recognition" in *Med Phys*, (1993), 20:1033–1041. Large sets of images that are routinely segmented and analyzed lend themselves to an extensive training set for more sophisticated neural networks and the complex technology of artificial intelligence, see Bezdek, et al., "Review of MR image segmentation techniques using patter recognition" in *Med Phys*, (1993), 20:1033–1041. Reliable, reproducible results that correctly delineate anatomical boundaries and define tissues comprised of partial volume signals are important to the methodology of this invention. Other methods are obvious to those skilled in the art and are also encompassed by the present invention.

EXAMPLE 4

Calculation of $T_2$ and Histogram Analysis of Gray Matter

Figure 3:
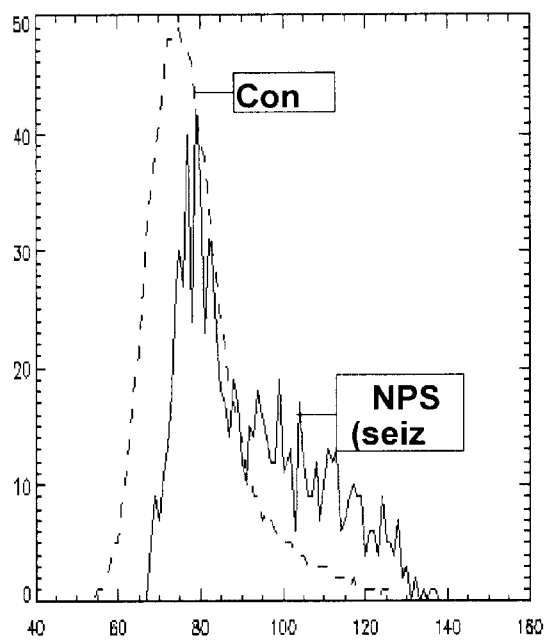
FIG. 3 is a graph showing typical results when segmented frontal gray matter (GM) histograms from one patient are compared with active NPSLE (seizures requiring hospitalization during the week prior to imaging) (solid line) to the histogram averaged from seven controls (dashed line)

Using this automated approach to select only pixels from pure gray matter, $T_2$ values were calculated from gray matter. $T_2$ maps were then produced where each pixel intensity reflects the $T_2$ arising from the corresponding tissue voxel. $T_2$ values are calculated using the Bloch equations for spin-spin relaxation on a pixel by pixel basis. $T_2$ data are fitted to an exponential curve using curve fitting algorithms available from the mathematical library in IDL, a mathematical computing language. However other computing environments could have also been used. Alternatively, for 2 points the logs of the equations are taken to produce a linear set of equations and a matrix of unknowns are solved by singular value decomposition fitting (IDL). $T_2$ is calculated using standard methods, but these could be uniexponential, biexponential, or polyexponential models (see Sibbitt, et al., "Spin-spin relaxation of brain tissues in systemic lupus erythematosus" in *Arth & Rheum*, (1995), 38:810–818, and Duncan, *Am J Neuroradiol*, (1996), 17:1805–1810. The limitation is primarily based on the number of TE variations which could vary from as few as two as in earlier conducted preliminary work to as many as four or greater based on the protocols used. However, important and powerful diagnostic information can be obtained from 2 TE variations, see Sibbitt, et al., "Spin-spin relaxation of brain tissues in systemic lupus erythematosus" in *Arth & Rheum*, (1995), 38:810–818. This information can be processed using average values and/or pixel histogram analysis. FIG. 3 shows typical results when segmented frontal GM histograms from one patient were compared with active NPSLE (seizures requiring hospitalization during the week prior to imaging) (solid line) to the histogram averaged from seven controls (dashed line). All brains were segmented as described in the Methods. The mean $T_2$ from the control histogram is 80.3 ms and the mean from the patient with NPSLE was 84.2 ms. It is clear that the elevation in $T_2$ of normal-appearing GM is due to both an overall increase in the $T_2$ of all pixels and a specific increase in a subpopulation with extremely high $T_2$ (>90 ms). It is likely that both the average value and the $T_2$ pixel distribution will have significant diagnostic value. These findings are consistent with multifocal breakdown in the blood-brain barrier resulting in vasogenic edema as well as other etiologies. Since focal lesions in NPSLE have different relaxation properties depending on etiology and reversibility, see Sibbitt, et al., "Spin-spin relaxation of brain tissues in systemic lupus erythematosus" in *Arth & Rheum*, (1995), 38:810–818, histogram analysis will permit more detailed study of both normal-appearing tissues and focal lesions.

EXAMPLE 5

Comparison of Automated and Manual Methods of $T_2$ Determination

Figure 4:
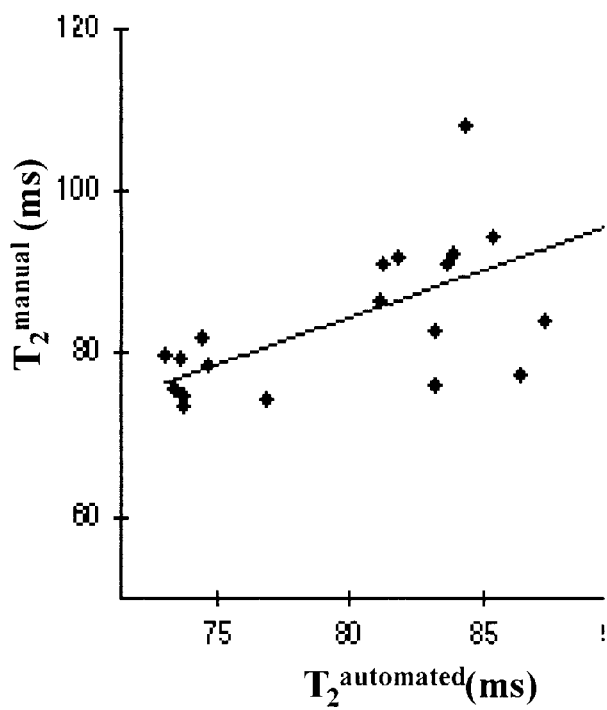
FIG. 4 is a graph comparing $T_2$ measured manually with the values obtained using a segmentation routine of the present invention.

The reliability of the automated methodology was determined by comparing $T_2$ measured manually as reported earlier, see Sibbitt, et al., "Spin-spin relaxation of brain tissues in systemic lupus erythematosus" in *Arth & Rheum*, (1995), 38:810–818, with the values obtained using a segmentation routine of the present invention, see FIG. 4. $T_2$ was calculated from the same images in 24 subjects. As summarized in FIG. 3 the Pearson Product Moment Correlation was r=0.64, p=0.002, see Petropoulos, et al., "Elevated $T_2$ of gray matter in systemic lupus erythematosus determined by automated segmentation and histogram analysis" in *Proc Int Soc Magn Reson Med 4th Scientific Meeting*, New York, (1996), the entire disclosure and contents of which is hereby incorporated by reference. Thus, these methods have confirmed that the $T_2$ of GM is increased specifically in those groups of NPSLE patients with active diffuse disease. The mean normal values determined from the automated method are slightly higher than those obtained from the manual method.

EXAMPLE 6

Confirmation of Exclusion of Partial Volume Effects

To ensure that the elevated $T_2$ findings were not the result of associated brain atrophy and inclusion of CSF into the $T_2$ calculation, the association between $T_2$ and brain atrophy was determined. Axial slices were selected which included lateral ventricles and calculated the ratio of cerebrospinal fluid volume to intracranial volume (CSF/ICV) as a measure of brain atrophy, see Paley, et al., "Cerebrospinal Fluid— Intracranial Volume Ratio Measurements in Patients with HIV Infection: CLASS Image Analysis Technique" in *Radiology*, (1994), 190:879–886. A poor correlation between CSF/ICV and $T_2$ ($r^2$=0.02) was confirming the measurement of elevated $T_2$ is the result of brain tissue changes rather than atrophy, see Petropoulos, et al., "Automated $T_2$ quantitation in Neuropsychiatric Lupus Erythematosus: a marker of active disease" in *J Magn Reson Imaging*, (1999), 9:39–43.

When an alternative semiquantitative atrophy scale is employed, again no correlation between the $T_2$ measurements and cerebral atrophy could be demonstrated.

EXAMPLE 7

Utility of Gray Matter $T_2$ Determination in SLE

The unanticipated, but exceptional power of this technology is demonstrated in systemic lupus erythematosus (SLE) and other diffuse brain diseases. SLE is an inflammatory disease characterized by intense autoimmune attack on the skin, joints, heart, lungs, kidneys, hematopoietic system, and the brain. Neuropsychiatric SLE (NPSLE) which affects up to 75% of SLE patients, see Adelman, et al., "The neuropsychiatric manifestations of systemic lupus erythematosus: an overview" in *Semin Arth Rheum*, (1986), 15:185, may display virtually any neurologic abnormality, including diffuse encephalopathy, psychiatric disturbances, dementia, delirium, affective disorders, anxiety syndromes, cranial neuropathies, cerebrovascular accidents, transverse myelitis, movement disorders, seizures, headaches, aseptic meningitis, pseudotumor cerebri, and lupoid sclerosis, see West, "Neuropsychiatric lupus" in *Rheum Dis Clinics N Am*, (1994), 20:129–158. Cognitive testing results are often abnormal and have been used to determine response to therapy, see Hanly, et al., "Cognitive impairment in patients with systemic lupus erythematosus" in *J Rheumatol*, (1992), 19:562–567, and Denburg, et al., "Corticosteroids and neuropsychological functioning in patients with systemic lupus erythematosus" in *Arthritis Rheum*, (1994), 37:1311–1320. However, cognitive testing is not necessarily objective or sensitive for differentiating active from previously active brain disease. One of the widely accepted criteria for measuring disease activity is the SLEDAI. However, this index is aimed at measuring systemic disease activity and includes data from the whole body rather than that isolated to the brain. A simple, objective measure of brain disease activity is a desperately needed goal for clinical practice and efforts to evaluate therapeutic options of NPSLE and other encephalopathies.

Figure 5:
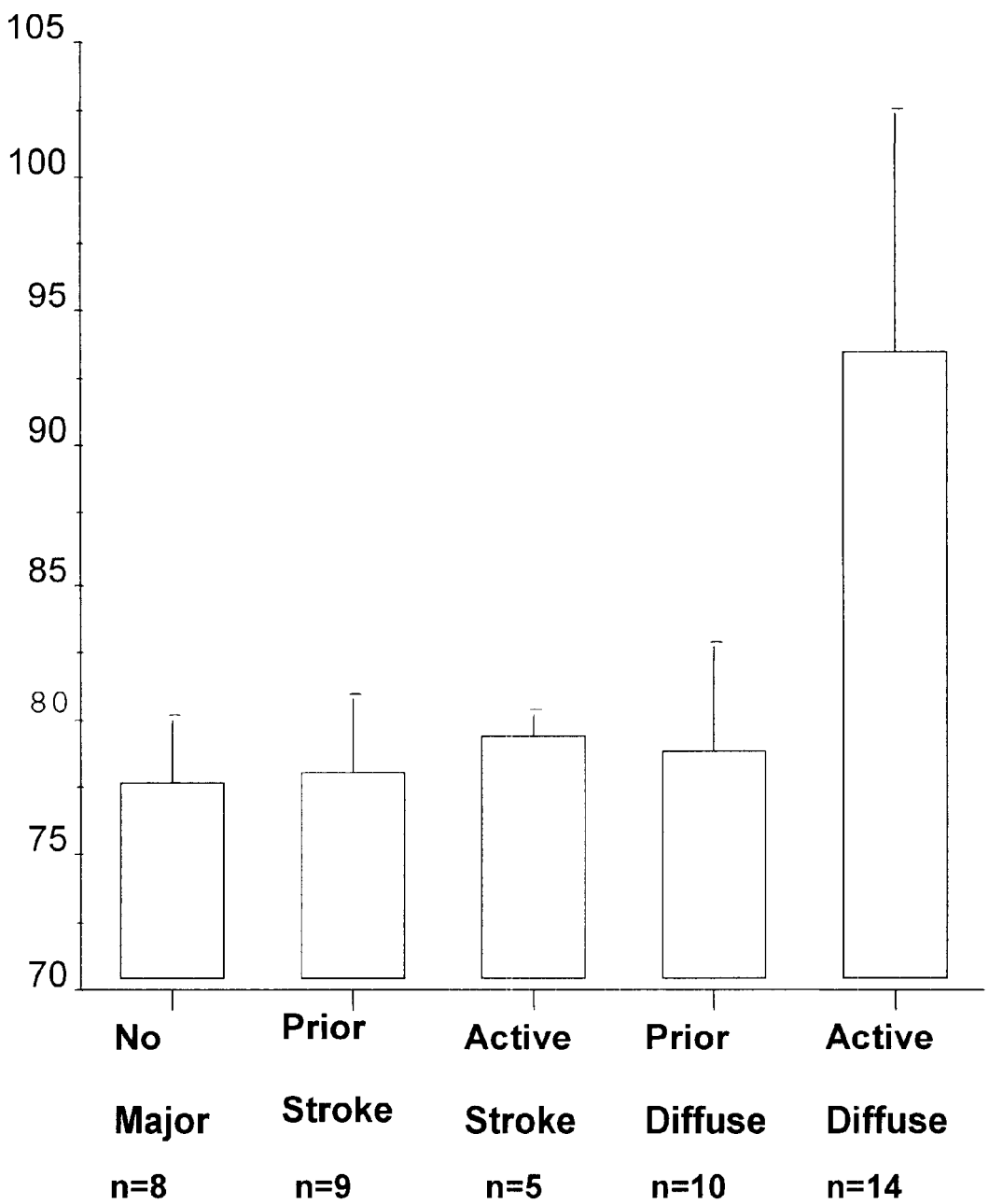
FIG. 5 is a bar graph illustrating T2 values from Lupus patients. In particular, those patients with active diffuse symptoms have significantly elevated T2 of GM compared with other less active and inactive forms of the disease. Also, patients who have had prior active diffuse disease but whose condition has resolved, show T2 values in the normal range.

$T_2$ is significantly elevated in normal-appearing gray matter (GM) of patients with active NPSLE, see Sibbitt, et al., "Spin-spin relaxation of brain tissues in systemic lupus erythematosus" in *Arth & Rheum*, (1995), 38:810–818. Elevated GM $T_2$, consistent with acute cortical injury, occurred in patients with acute major neuropsychiatric manifestations (diffuse NPSLE=seizures, psychosis, coma, delirium). The means (SD) for $T_2$ (diffuse NPSLE)=92.7 (6.3)ms and for $T_2$ (normal)=78.9 (3.1)ms; p=0.0002, see FIG. 5. To determine the time course of these changes two patients were studied with elevated $T_2$ during periods of active diffuse NPSLE and subsequent inactive NPSLE. It was found that $T_2$ elevations ($T_2$=86, 87 ms respectively) accompanied active NPSLE and returned to normal levels ($T_2$=79, 77 ms respectively) with resolution of the neurologic complaints, indicating that elevated $T_2$ in GM is a reversible process closely associated with neurologic symptoms. The entire data set shows that, while specifically excluding patients with overt stroke, elevated $T_2$ of GM in SLE is a sensitive indicator of active major NPSLE (>90% sensitivity; >90% specificity).

The etiology of increased GM $T_2$ in NPSLE is unknown, although ischemia, cerebral edema, blood-brain barrier breakdown, or direct autoimmune attack is suspected. Cerebral edema, which can induce neuronal injury by both neurocytotoxic and vascular mechanisms, see Kimelberg, "Current concepts of brain edema: Review of laboratory investigations" in *J Neurosurg* (1995), 83:1051–1059, may be the most likely etiology of increased GM $T_2$, see Sibbitt, et al., "Spin-spin relaxation of brain tissues in systemic lupus erythematosus" in *Arth & Rheum*, (1995), 38:810–818. Thus, prevention and treatment of cerebral edema may be critical for protecting and salvaging neurons during NPSLE attacks. Therefore, determination of $T_2$ of gray matter, and perhaps of lesions, may be a critically sensitive method for the diagnosis of NPSLE. The automated method described above permits the timely diagnosis of this entity.

EXAMPLE 8

Utility of $T_2$ and the Determination of Disease subtype in NPSLE

There is evidence that anti-ribosomal P antibodies are associated primarily with lupus psychosis, but not generalized seizures, see Isshi, et al., "Association of anti-ribosomal P protein antibodies with neuropsychiatric systemic lupus erythematosus" in *Arthritis Rheum*, (1996), 39:1483–1490. To determine whether there were a corresponding difference in cerebral edema, patients with different forms of active diffuse NPSLE, organic psychosis or generalized seizures, were compared in order to determine the presence of fundamental differences in brain chemistry or structure. The results are shown in Table 1 below:

TABLE 1

|  | Normals n = 23 | Generalized Seizures N = 8 | Organic Psychosis n = 6 |
|---|---|---|---|
| Reversible Lesions | 0.00 ± 0.00 | 2.89 ± 2.42 | 0.00 ± 0.00 |
| Gray Matter T2 | 78.1 ± 2.2 | 94.0 ± 10.0 | 86.2 ± 8.8 |

$T_2$ was further elevated in patients with generalized seizures compared to those with organic psychosis (normal, 78.1 ms (±2.2 ms SD); seizures, 94.0 (±10.0); psychosis, 86.2 (±8.8)). Furthermore, reversible focal lesions were entirely isolated to the group of patients who had experienced recent generalized seizures. Thus, generalized seizures appears to represent a greater acute injury to the brain, resulting in greater elevations in GM $T_2$, and reversible focal lesions. Organic psychosis is similar, but with less elevation in $T_2$ and no acute focal lesions indicating that $T_2$ can also be used to separate disease sub-types.

EXAMPLE 9

Utility of $T_2$ of Focal Lesions in NPSLE

NPSLE is characterized by several forms of brain injury which are visible on MRI including focal lesions. An attempt was made to determine whether $T_2$ could be used to segregate different types of lesions. $T_2$ values were increased in all forms of cerebral lesions in SLE, see Sibbitt, et al., "Spin-spin relaxation of brain tissues in systemic lupus erythematosus" in *Arth & Rheum*, (1995), 38:810–818. The difference between reversible lesions, irreversible focal lesions, and obvious infarct is highly significant (deep white matter=68.5 ms (±5.2 ms; n=54), reversible lesions 107.2

(±12.2; n=31), irreversible lesions 84.7 (±10.7; n=133), old infarct 181.6 (±63.6; n=12)), indicating that the microenvironments of these lesions were different, presumably from differences in micropathology. Most likely, the reversible lesions represent focal edema secondary to vasculopathy while the focal irreversible lesions represent small infarctions with secondary gliosis. Large infarctions have a marked effect on $T_2$, suggesting focal atrophy and replacement of tissue with fluid. The use of $T_2$ values from individual lesions may allow a degree of discrimination between the different types of lesions, but is limited by the very large standard deviations of each group, reflecting considerable overlap between the $T_2$ of the different lesions. This is consistent with prior observations demonstrating that lesions of very different micropathology can have similar spin-spin relaxation characteristics, see, Karlik, et al., "NMR studies in experimental allergic encephalomyelitis: Factors which contribute to $T_1$ and $T_2$ values." in *Magn Reson Med*, (1990) 14:1–11. However, pixel histogram analysis of such lesions may permit accurate discrimination between these lesions, which would be of considerable diagnostic benefit. Thus, segmentation and analysis of conventional MR images as noted above may have powerful diagnostic and clinical management value.

EXAMPLE 10

Utility of Gray Matter $T_2$ in Hepatic Encephalopathy (HE)

MR imaging of HE does not detect specific changes that correlate with the degree of encephalopathy. However, since preterminal hepatic encephalopathy is associated with cerebral edema, it is hypothesized that milder degrees of this disorder would also be associated with subtle degrees of increased $T_2$ of GM, consistent with mild degrees of cerebral edema. Studying four HE patients using the manual method it was determined $T_2$ values of 76.27 (Grade 0 HE), 77.07 (Grade 1 HE), 87.7 (Grade 2 HE), and 81.04 (Grade 2 HE) (normal controls=78.9). These data suggest that HE is characterized by cerebral edema, particularly at Grade II and that cerebral edema may be a significant contributing factor in HE, even in lower grades of HE, increasing the diagnostic specificity for MR imaging for this metabolic disorder.

This observation suggests that the extensive results regarding the correlation between $T_2$ and brain disease activity are not confined to NPSLE alone but are relevant to other diseases.

EXAMPLE 11

Utility of $T_2$ of Brain in Head Trauma

Using the automated analysis technique, two subjects were examined who had suffered traumatic brain injury arising from motor vehicle accidents. Preliminary results show that when measured 3 months after the injury their $T_2$ values were still markedly elevated, 83.9 ms and 83.1 ms respectively. This indicates that precise measures of gray or white matter $T_2$ detect injury not obvious by conventional imaging.

EXAMPLE 12

Utility of $T_2$ of Brain in Multiple Sclerosis $T_2$ of gray matter in 2 patients with secondary progressive multiple sclerosis has also been measured. In one of these patients the mean $T_2$ was elevated (84.3 ms) while in the second the mean $T_2$ was closer to normal (81.1 ms). The time course and clinical significance of these elevated values remains to be determined. This suggests that this technique may also be useful in those diseases previously considered to be primarily white matter disease.

EXAMPLE 13

Utility of $T_2$ of Brain in ALS

Nine patients who fulfilled the WFN-EI Escorial Criteria for definite diagnosis of ALS were compared with ten age-matched normal controls. Subjects were scanned at 1.5 Tesla on a GE Signal clinical scanner. Dual echo acquisitions (TE=30/100 ms, TR=2800 ms, 3 mm slices) were used to calculate $T_2$ from three locations: occipital white matter (WM), fronto-parietal gray mater (GM), and MC (bilateral). The images were segmented to delineate MC, to remove CSF from sampled areas, and to determine the CSF to intracranial volume (CSF/ICV) ration for assessment of atrophy.

$T_2$ was calculated from the proton density (PD) and $T_2$-weighted images corresponding to each tissue type using the following equations (1) and (2):

$$I_1 = k * I_o * e^{-(te_1/T_2)} \quad (1)$$

$$I_2 = k * I_o * e^{-(te_2/T_2)} \quad (2)$$

where k is a constant, $I_o$ is the intensity at time zero, and te is the echo time. Equations (1) and (2) were solved using singular value decomposition fitting routines available in IDL (Research Systems, Inc., Boulder, Colo.). Two point determination of $T_2$ provides only an estimate of true $T_2$, but is reproducible and may be calculated from conventional MRI acquisitions.

Images were segmented using an unsupervised k-means classification algorithm available in Khoros (Khoral Research, Inc., Albuquerque, N.Mex.). The segmentation produced a labeled image which allowed the user to choose a specific tissue type and exclude areas containing CSF and partial volume contribution form CSF. $T_2$ was calculated on a pixel-by-pixel basis form the intensities of the PD/$T_2$-weighted images corresponding to each tissue type.

Atrophy Assessment

Atrophy may cause sulcal widening, allowing CSF to intercalate with GM and cause falsely elevated $T_2$. In order to control this effect CSF/ICV was calculated by segmenting the PD/$T_2$-weighted image pairs and measuring volumes for brain tissue, CSF, and partial volume CSF. ICV was calculated as a sum of the volumes and one half of the total partial volume was added to the CSF total.

Results

A comparison means was done by independent t-tests using SPSS (Macintosh version 6.1, Chicago, Ill.) and the results are listed in Table 2 below:

TABLE 2

| Brain Tissue | Control | ALS | Significance |
| --- | --- | --- | --- |
| GM | 74.6 ± 2.5 ms | 77.5 ± 5.8 ms | p = 0.16 |
| WM | 72.7 ± 4.2 ms | 74.5 ± 2.4 ms | p = 0.27 |
| MC | 84.5 ± 2.9 ms | 90.5 ± 6.0 ms | p = 0.01 |

Figure 6:
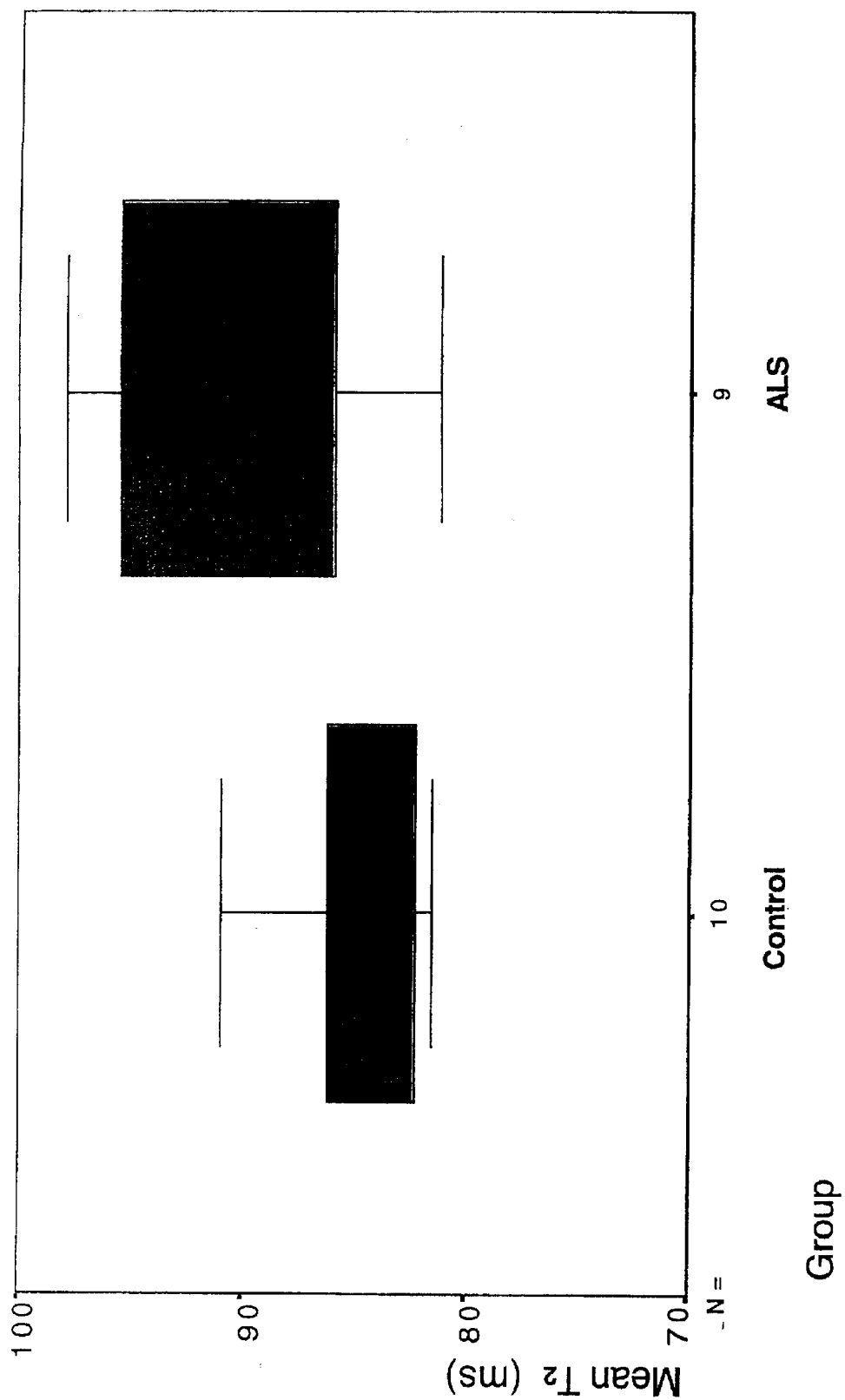
FIG. 6 is a graph of Mean $T_2$ for motor cortex samples from a control group and a group of individuals with ALS.
Figure 7:
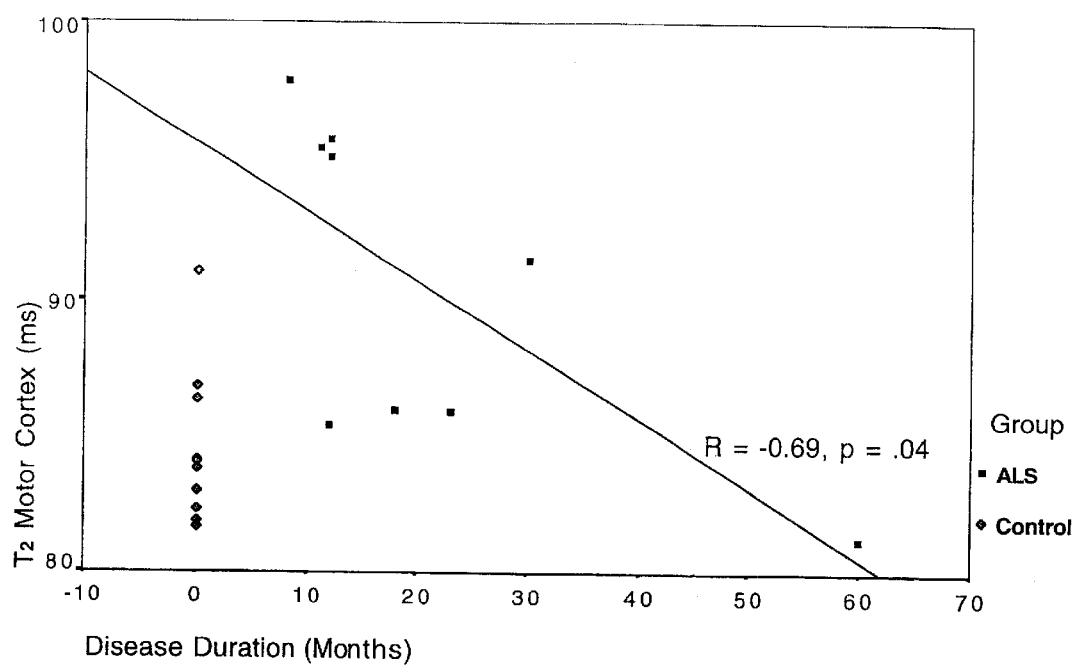
FIG. 7 is a graph illustrating correlation of $T_2$ with disease duration for one group of test subjects.

No difference was $T_2$ was found between groups for WM and GM. However, $T_2$ in MC was significantly elevated, as shown in FIG. 6, and negatively correlated with disease duration, as shown in FIG. 7. Patients with longer disease duration had elevated $T_2$ compared with controls Patients with longer disease duration had $T_2$ values in the normal range. Moreover, $T_2$ was not associated with the increased atrophy seen in normal aging and in patients with ALS (r=0.35, p=0.35).

Conclusions

Elevated $T_2$ is associated with pathologic processes, including infarct, inflammation, edema (intracellular or extracellular), and gliosis. The above described data shows that $T_2$ in MC in ALS is elevated, suggesting increased disease activity or injury, possibly with associated gliosis. Abnormal $T_2$ values were not seen in other parts of the brain, possibly suggesting a predominating localized process, consistent with clinical presentation. Patients with short disease duration showed elevated $T_2$ which maybe caused by injury or greater activity early in disease progression. Patients with longer duration have relaxation times similar to controls, possibly suggesting decrease of activity in later stages. Given the difficulty of management of ALS, $T_2$ measurements may provide useful data for staging the disease. In conjunction with complementary analysis such as Magnetic Resonance Spectroscopy, quantitative MR may extend the clinical profile of patients with ALS and assist in disease classification and monitoring treatment.

EXAMPLE 14

Methods

Subjects. Patients were recruited from a Neuromuscular Disease clinic. 14 patients with clinically definite ALS and one with clinically probable ALS by the El Escorial criteria were studied and compared with 18 age-matched controls. This latter patient was subsequently classified as definite ALS during a follow up examination soon after scanning. Exclusion criteria included metal implants that contraindicated MR studies, claustrophobia, or the inability to lie still and supine for the duration of the examination (approximately 1 hour). The ages of the patients with ALS ranged from 40–81 years (mean age 59.3±13.0) and of the controls 38–75 years (mean age 57.3±10.4). Twelve patients had limb onset and four had bulbar onset. Disease duration was defined as the time between identifying the first symptom of ALS and the date of scan. All studies were approved by the Institutional Review Board. Written informed consent was obtained from each subject prior to study.

Magnetic Resonance Imaging All MR imaging acquisitions employed a 1.5 Tesla scanner (GE Signa 5.4, General Electric Medical Systems, Milwaukee, Wis.). Imaging sequences included a conventional dual echo axial series (TE=30/100 ms, TR=2800 ms, 3 mm slice/1 mm gap) and a $T_1$-weighted fast Spoiled Grass series acquired using 3 mm thick contiguous slices (TE=6.9, TR=17.7, flip angle=$25_i$).

Segmentation. Since different tissue types such as GM, WM, and cerebrospinal fluid (CSF) have different $T_2$ values and the primary intent was to measure $T_2$ in pure GM, automated segmentation was used to select pure GM while specifically excluding data from voxels which contained non-GM tissue types, see Petropoulos, et al., "Semi-automated segmentation of dual echo MR images" in *Proc IEEE EBMS*, (1998), 20:602–604. This is particularly important since CSF has a considerably longer $T_2$ than GM, and the inclusion of pixels with even a small fraction of CSF would erroneously elevate the apparent $T_2$ of that voxel. Thus, the segmentation identified pixels corresponding to pure CSF, GM, and WM as well as those comprising mixed tissue type (partial volume) pixels, see Petropoulos, et al., "Semi-automated segmentation of dual echo MR images" in *Proc IEEE EBMS*, (1 998), 20:602–604. $T_2$ measurements were made on the pure GM pixels. The region of interest (ROI) was extracted from the segmented image by masking off the motor cortex. As a control region, normal-appearing GM in the occipitoparietal region was examined to determine whether changes in $T_2$ were localized to tissue implicated in the clinical presentation or were more generalized.

$T_2$ determination. $T_2$ values were determined using a two-point calculation for each pixel for each of the ROIs using the registered proton density (PD) and $T_2$-weighted pair of images as described previously, see Petropoulos, et al, "Automated $T_2$ quantitation in Neuropsychiatric Lupus Erythematosus: a marker of active disease" in *J Magn Reson Imaging*, (1999), 9:39–43.

Atrophy. Because the $T_2$ measurements were from GM adjacent to CSF boundaries, it was determined if whether atrophy had an effect on the measurements of $T_2$. Global atrophy in each patient was assessed quantitatively using the CSF to intracranial volume ratio (CSF/ICV), a sensitive measure of atrophy, see Paley, et al., "Cerebrospinal fluid-intracranial volume ratio measurements in patients with HIV infection: CLASS image analysis technique" in *Radiology*, (1994), 190:879–886. Values for CSF and ICV were calculated by summing the total number of pixels corresponding to each tissue type following segmentation, i.e., the total number of pixels corresponding to CSF was divided by the total number of pixels corresponding to parenchyma and CSF to produce this atrophy index. The correlation coefficient between atrophy and $T_2$ was then determined to confirm that any alterations in $T_2$ reflected bulk tissue changes and not a partial volume contribution of CSF.

MRI Assessment. Signal drop in the motor cortex and corticospinal tract (CST) hyperintensities in $T_1$ and $T_2$-weighted images have been reported in ALS. Accordingly, each imaging series was assessed by a neuroradiologist blinded to subject group or age. Each abnormality received a score based on a simple system: not present (score=0), mild (1), moderate (2). All statistical analyses were carried out using SAS (v 6.12, Cary, N.C.).

Results

Figure 8:
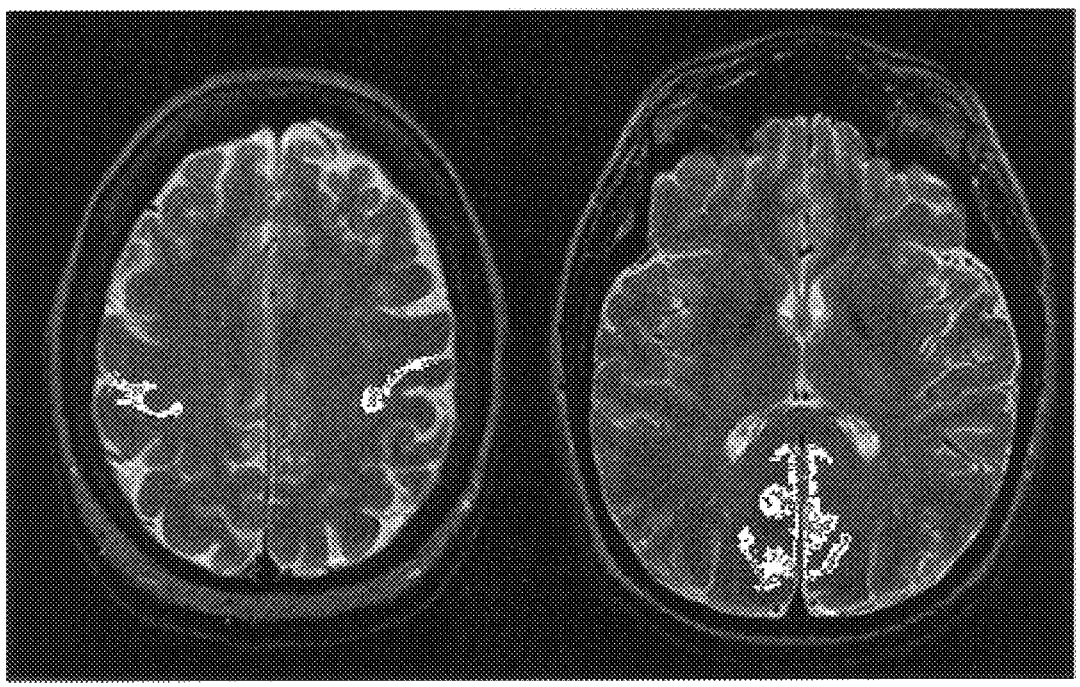
FIG. 8 illustrates two $T_2$-weighted images overlaid with a) segmentation of pure motor cortex GM (left image) and b) segmentation of pure gray matter in the occipitoparietal lobe (right image)

The labeled image results of the initial segmentation are shown in FIG. 8. The pixels representing pure GM from the motor cortex and from the occipitoparietal region are highlighted.

The group results of the $T_2$ analysis are summarized in Table 3.

TABLE 3

| Brain Tissue | Control | ALS | Significance |
| --- | --- | --- | --- |
| $T_2$ Motor Cortex (ms) | 84.5 ± 2.9 | 90.4 ± 5.0 | p = 0.001 |
| $T_2$ Occipital Gray (ms) | 74.5 ± 2.8 | 73.9 ± 2.8 | p = 0.526 |

Figure 9:
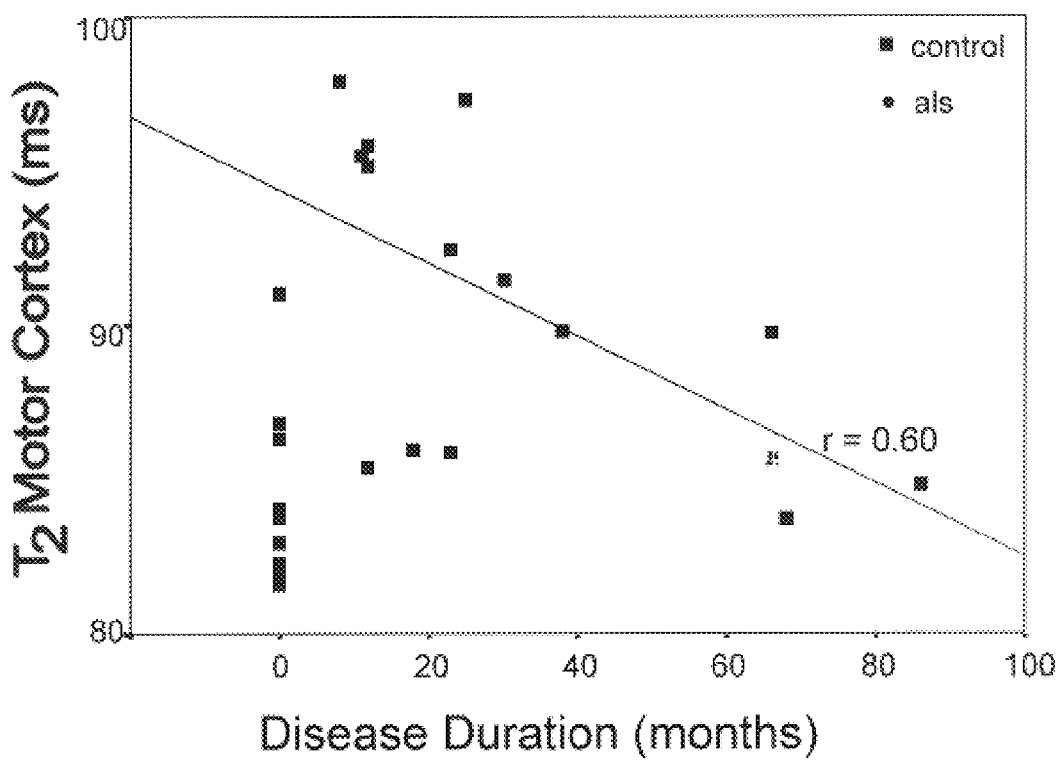
FIG. 9 is a graph illustrating correlation of $T_2$ with disease duration for a second group of test subjects.

The initial finding was that the motor cortex $T_2$ of patients with ALS (90.4±5.0 ms) was significantly higher than controls (84.5±2.9 ms) as determined by a 2-sample t-test (p=0.001). Secondly, motor cortex $T_2$ of patients with ALS was negatively correlated with disease duration (r=–0.6, p=0.04), see FIG. 9. $T_2$ was elevated in patients with a short disease duration, while those with a longer duration had values in the motor cortex similar to those of controls. In contrast, the $T_2$ measurements of occipital GM produced no significant differences between ALS and control groups (p=0.53). There was no correlation with $T_2$ measurement and onset type. New paragraph!

The results of the visual image interpretation are summarized in Table 4 below:

TABLE 4

| Brain Tissue | Control | ALS | Significance |
|---|---|---|---|
| CST Hyperintensity - PD | 0.00 ± 0.0 | 0.73 ± 0.6 | p < 0.001 |
| CST Hyperintensity - $T_2$ | 0.81 ± 0.4 | 1.08 ± 0.4 | p = 0.06 |
| $T_2$ Signal Drop | 0.79 ± 0.6 | 1.54 ± 0.6 | p = 0.002 |

Decreased signal intensity was noted in the motor strip of both controls and patients with ALS. However, the abnormality score was higher in the ALS cohort (p=0.002). Since hypointensity of the motor cortex on MRI has been associated with age, see Hirai, et al., T, "$T_2$ shortening in the motor cortex: effect of aging and cerebrovascular diseases" in *Radiology*, (1996), 199:799–803, analysis of variance was used to show that after correcting for age, the result was still significant (p=0.004).

Increased signal intensity was noted in the posterior limb of the internal capsule, which may represent the parietopontine tract, on $T_2$-weighted images of both ALS patients (12/15) and controls (15/18). However, these hyperintensities appeared more frequently and were more pronounced in ALS patients than controls (p=0.06). Secondly, eight ALS patients also had very subtle areas of increased signal intensity in the same anatomical region on the corresponding proton density images, while none were noted on the control images.

There was no significant difference in atrophy between groups as assessed by CSF/ICV (p=0.34). Further, correlation of CSF/ICV with motor cortex $T_2$ from patients did not reach significance (r=0.37, p=0.11), indicating that our findings of elevated $T_2$ were not due to increased atrophy.

Discussion

Cranial MRI is commonly used in assessment of patients with suspected ALS. However, its primary role has been to exclude other causes of neurological symptoms. The present study demonstrates that quantitative analysis of MR images reveals potentially valuable data regarding disease progress in ALS. Our finding of elevated $T_2$ in most patients with disease duration between 9 and 40 months, and lower values in patients with more prolonged disease, suggests an increase in the disease activity, possibly associated with onset.

Elevated $T_2$ often indicates edema, suggesting inflammation. Therefore, higher motor cortex $T_2$ in those patients with shorter disease duration may indicate inflammation due to neuronal degeneration, perhaps accompanied by edema or reactive gliosis, which has been reported in post mortem histological studies in ALS patients, see Oba, et al., "Amyotrophic Lateral Sclerosis: $T_2$ shortening in motor cortex at MR Imaging" in *Radiology*, (1993), 19:843–846; and Kamo, et al., "A distinctive distribution of reactive astroglia in the precentral cortex in amyotrophic lateral sclerosis" in *Acta Neuropathol*, (1987), 74:33–38. Accordingly, lower $T_2$ values in those patients with longer disease duration may reflect decreasing inflammation. One possibility to explain the lower $T_2$ values in those patients is that after cellular debris is removed by macrophage activity, these cells enter a quiescent state, filling the space left by the neuronal demise. Indeed, there is evidence to indicate that there is microglial response in ALS and that it occurs in the absence of monocyte trafficking, see Guilian, et al., "Cell surface morphology identifies microglia as a distinct class of mononuclear phagocyte" *J Neurosci*, (1995), 15:7712–7726.

A second possible mechanism involves cortical hypointensities which have been visualized in motor cortex of some ALS patients. In fact, our study found this MRI abnormality to be more frequent and more pronounced in ALS patients. Such signal drop has been attributed to iron deposition, see Ishikawa, et al., "Signal loss in the motor cortex on magnetic resonance images in Amyotrophic Lateral Sclerosis" in *Ann Neurol*, (1993), 33:218–222; Oba, et al., "Amyotrophic Lateral Sclerosis: $T_2$ shortening in motor cortex at MR Imaging" in *Radiology*, (1993), 19:843–846; Imon, et al., "Low intensity areas observed on $T_2$-weighted magnetic resonance imaging of the cerebral cortex in various neurological diseases" in *J Neurol Sci*, (1995), 134 (suppl):27–32; and Hirai, et al., "$T_2$ shortening in the motor cortex: effect of aging and cerebrovascular diseases" in *Radiology*, (1996), 199:799–803. However, the diagnostic usefulness of this observation is compromised by similar hypointensities in some normal controls. Therefore, visual assessment of brain is not a reliable indicator of upper motor neuron involvement and hence not a reliable diagnostic tool for ALS. Although similar findings were noted in the current study, these locations were excluded by segmentation prior to $T_2$ calculation. Thus, our $T_2$ findings likely reflect a more subtle change in adjacent areas, possibly indicating microscopic injury. Subsequently, iron deposition to an extent that does not result in visible change and is not excluded by segmentation may also result in lower $T_2$.

From a radiological perspective, elevated $T_2$ is usually visualized as frank lesions seen on $T_2$-weighted images. Although bilateral hyperintensities in the pyramidal tract have been reported in ALS, such findings are controversial, see Imon, et al., "Low intensity areas observed on $T_2$-weighted magnetic resonance imaging of the cerebral cortex in various neurological diseases" in *J Neurol Sci*, (1995), 134 (suppl): 27–32; and Hirai, et al., "$T_2$ shortening in the motor cortex: effect of aging and cerebrovascular diseases" in *Radiology*, (1996), 199:799–803. Hyperintensity is commonly identified in the region of the posterior internal capsule on $T_2$-weighted images in many individuals, including controls, and this may represent the parietopontine tract. As with some earlier investigations, it was found to be important to consider only areas that were hyperintense on both early and late echo images (proton density and $T_2$-weighted), see Cheung, et al., "Amyotrophic Lateral Sclerosis: correlation of clinical and MR imaging findings" in *Radiology*, (1995), 194:263–270; and Mascalchi, et al., "Corticospinal tract degeneration in motor neuron disease" in *AJNR Am J Neuroradiol*, (1995), 16:878–880. Using this criterion, abnormalities were detected only in ALS patients. Specificity of internal capsule hyperintensity on proton density images is therefore high. However, the sensitivity of these findings remains low, and it should be emphasized that imaging findings are very subtle.

Previous efforts to identify a role for quantitative $T_2$ measurements in ALS have proven fruitless, see Hofmann, et al., "The corticospinal tract in amyotrophic lateral sclerosis: an MRI study" in *Neuroradiology*, (1998), 40:71–75; and Tanabe, et al., "Reduced MTR in the corticospinal tract and normal $T_2$ in Amyotrophic Lateral Sclerosis" in *Magn Reson Imaging*, (1998), 16:1163–1169. However, since $T_2$ is especially sensitive to inclusion of pixels which represent mixed tissue type, particular care must be taken to sample only pure tissue. Accordingly, thin image slices were employed and automated segmentation was employed to select pixels corresponding to unambiguous (GM) tissue.

The correlation of motor cortex $T_2$ with disease duration suggests a non-invasive method for determining upper motor neuron involvement early in the course of this disease. Further longitudinal studies employing serial scanning of patients with suspected ALS i.e., patients who are yet to display upper motor neuron symptoms, are required to verify and extend these preliminary results. However, although most data points follow a well-defined linear pattern possibly reflecting the progressive nature of ALS, three apparently do not and deserve some comment. Interpretations of this observation include an unreliable diagnosis date and hence unreliable disease duration, or a rapid disease progression that would distinguish them from the remainder of the cohort, or both. It should be noted that two of these patients suffered a rapidly progressive form of disease. Thus, given the somewhat subjective guidelines for diagnosis, it could easily be that individual effective disease durations could be underestimated.

Conclusion

In conclusion, the above data shows that there are $T_2$ differences in the motor strip of patients with ALS compared with controls. The above data also show that these $T_2$ values are abnormally high in patients who are in a relatively early stage of disease. It is possible that these results reflect pathological activity in ALS.

Since $T_2$ measurements may be made from standard clinical imaging sequences which are available on all MR scanners, this approach offers the opportunity for widespread implementation. Further, since conventional sequences are employed, it might be possible to retrospectively analyze MRI scans acquired prior to formal diagnosis of ALS when the cause of symptoms has not been determined, adding further objective data for diagnosis. Given that worldwide, the mean time of onset of symptoms to confirmation of diagnosis of ALS is 16–18 months, see Gelinas, "Conceptual approach to diagnostic delay in ALS: a United States perspective" in *Neurology*, (1999), 53:S17–S19, quantitative $T_2$ measurements may provide the basis for a tool to assist physicians in diagnosing and following this debilitating disease.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for determining whether an individual has a central nervous system disease or injury comprising:
   obtaining a $T_2$ measurement for at least one brain tissue sample from an individual using an MRI technique;
   determining if said $T_2$ measurement indicates the presence of a central nervous system disease or injury in the individual.

2. The method of claim 1, wherein said brain tissue sample comprises a cortex gray matter sample.

3. The method of claim 1, wherein said $T_2$ measurement is obtained using an MRI field strength of 1.5 Tesla and the individual is determined to have a central nervous system disease or injury if said $T_2$ measurement exceeds about 88 ms.

4. The method of claim 1, wherein said $T_2$ measurement is obtained using an MRI field strength of 1.5 Tesla and the individual is determined to have a central nervous system disease or injury if said $T_2$ measurement exceeds about 90 ms.

5. The method of claim 1, wherein said brain sample is obtained using a segmentation technique.

6. A method for determining whether an individual has a central nervous system disease or injury comprising:

obtaining a first $T_2$ measurement using an MRI technique for a brain tissue sample from the individual at a first time;
   obtaining a second $T_2$ measurement using an MRI technique for said brain tissue sample from the individual at a second time; and
   comparing said second $T_2$ measurement to said first $T_2$ measurement to determine whether the individual has a central nervous system disease or injury.

7. The method of claim 6, wherein said first brain tissue sample comprises a cortex gray matter sample and said second brain tissue sample comprises a cortex sample.

8. The method of claim 6, wherein the individual is determined to have a central nervous system disease or injury if said second $T_2$ measurement exceeds said first $T_2$ measurement.

9. The method of claim 6, wherein the individual is determined to be recovering from a nervous system disease or injury if said second $T_2$ measurement is less than said first $T_2$ measurement.

10. The method of claim 6, wherein said brain tissue sample is obtained using a segmentation technique.

11. A method for determining the effectiveness of a treatment for a central nervous system disease or injury comprising:
    obtaining a first $T_2$ measurement using an MRI technique for a brain tissue sample from an individual at a first time;
    administering a first treatment to an individual;
    obtaining a second $T_2$ measurement using said MRI technique for said brain tissue sample from the individual after administering said first treatment; and
    comparing said second $T_2$ measurement to said first $T_2$ measurement.

12. The method of claim 11, wherein said first brain tissue sample comprises a cortex gray matter sample and said second brain tissue sample comprises a cortex gray matter sample.

13. The method of claim 11, wherein the said treatment with said administered first treatment is determined to be effective if said second $T_2$ measurement is less than said first $T_2$ measurement.

14. The method of claim 11, further comprising:
    administering a second treatment to the individual after obtaining said second $T_2$ measurement; and
    obtaining a third $T_2$ measurement using an MRI technique for said brain tissue sample from the individual after administering said second treatment; and
    comparing said third $T_2$ measurement to at least one $T_2$ measurement selected from the group consisting of said first $T_2$ measurement and said second $T_2$ measurement.

15. The method of claim 14, wherein the said treatment with said administered first treatment is determined to be effective if said third $T_2$ measurement is less than said first $T_2$ measurement.

16. The method of claim 14, wherein the said treatment with said administered second treatment is determined to be effective if said third $T_2$ measurement is less than said second $T_2$ measurement.

17. The method of claim 11, wherein said administered first treatment and said administered second treatment comprise the same treatment.

18. The method of claim 11, wherein said brain tissue sample is obtained using a segmentation technique.

* * * * *